United States Patent
Yoshimura

(10) Patent No.: US 10,444,209 B2
(45) Date of Patent: Oct. 15, 2019

(54) EXHAUST GAS MEASURING SYSTEM

(71) Applicant: HORIBA, Ltd., Kyoto (JP)

(72) Inventor: Tomoshi Yoshimura, Kyoto (JP)

(73) Assignee: HORIBA, LTD., Kyoto (JP)

(*) Notice: Subject to any disclaimer, the term of this patent is extended or adjusted under 35 U.S.C. 154(b) by 227 days.

(21) Appl. No.: 15/364,976

(22) Filed: Nov. 30, 2016

(65) Prior Publication Data

US 2017/0168033 A1    Jun. 15, 2017

(30) Foreign Application Priority Data

Dec. 15, 2015 (JP) .................. 2015-244176

(51) Int. Cl.
*G01N 33/00* (2006.01)
*F01N 3/033* (2006.01)
(Continued)

(52) U.S. Cl.
CPC ......... *G01N 33/0006* (2013.01); *F01N 3/033* (2013.01); *F01N 11/00* (2013.01); *F01N 13/008* (2013.01); *G01L 27/002* (2013.01); *G01N 1/2252* (2013.01); *F01N 2560/022* (2013.01); *F01N 2560/023* (2013.01);
(Continued)

(58) Field of Classification Search
CPC ..... G01N 33/0006; F01N 11/00; F01N 3/033; F01N 13/008; F01N 2560/08; F01N 2560/022; F01N 2560/026; F01N 2560/023; F01N 2560/028; G01L 27/002
See application file for complete search history.

(56) References Cited

U.S. PATENT DOCUMENTS 9,909,473 B2 * 3/2018 Martin ................. F01N 11/002
2004/0064243 A1 * 4/2004 Nakamura ............ F01N 13/008
701/114
(Continued)

FOREIGN PATENT DOCUMENTS

| JP | 07-146235 A | 6/1995 |
| JP | 2002-214082 A | 7/2002 |
| JP | 2004-361241 A | 12/2004 |

OTHER PUBLICATIONS

EESR dated Mar. 14, 2017 issued for European Patent Application No. 16 201 097.9, 5 pgs.

*Primary Examiner* — Stephanie E Bloss
(74) *Attorney, Agent, or Firm* — Brooks Kushman P.C.

(57) ABSTRACT

In order to provide an exhaust gas measuring system capable of more accurately correcting errors in measurement results caused by response delays of exhaust gas measuring devices, and the like, the exhaust gas measuring system is adapted to include: a sampling pipe adapted to, from a lead-out port, lead out exhaust gas introduced from an introduction port; one or more types of exhaust gas measuring devices that are connected to the lead-out port and measure predetermined physical quantities related to the exhaust gas flowing through the sampling pipe; a correction device adapted to correct measurement results by the exhaust gas measuring devices; and a pressure sensor adapted to measure the pressure inside the sampling pipe, in which the correction device corrects errors in the measurement results, which are caused by response delays, with the measured pressure by the pressure sensor as a parameter.

9 Claims, 6 Drawing Sheets

(51) Int. Cl.
  *F01N 11/00* (2006.01)
  *F01N 13/00* (2010.01)
  *G01L 27/00* (2006.01)
  *G01N 1/22* (2006.01)
(52) U.S. Cl.
  CPC .. *F01N 2560/026* (2013.01); *F01N 2560/028* (2013.01); *F01N 2560/08* (2013.01)

(56) References Cited

U.S. PATENT DOCUMENTS

| | | | |
|---|---|---|---|
| 2009/0188309 A1* | 7/2009 | Hartimath | F01N 3/208 73/114.76 |
| 2010/0286930 A1* | 11/2010 | Onishi | F01N 3/021 702/24 |
| 2011/0054760 A1* | 3/2011 | Ogawa | F02B 25/145 701/102 |
| 2011/0106466 A1* | 5/2011 | Furmanski | A61M 1/3653 702/51 |
| 2011/0168129 A1* | 7/2011 | Kurtz | F02D 19/061 123/294 |
| 2011/0214422 A1* | 9/2011 | VanDyne | F01N 3/10 60/607 |
| 2012/0078532 A1* | 3/2012 | Forsyth | G01N 21/274 702/24 |
| 2014/0165692 A1* | 6/2014 | Rannow | F15B 19/002 73/1.63 |
| 2014/0174073 A1* | 6/2014 | Karnik | F02B 37/18 60/602 |
| 2016/0131012 A1* | 5/2016 | Prospero | F02D 41/029 60/295 |
| 2016/0131550 A1* | 5/2016 | Besling | G01L 9/0072 702/98 |
| 2016/0138447 A1* | 5/2016 | Martin | F01N 11/002 60/274 |

* cited by examiner

| SAMPLE ENTRANCE PRESSURE | RESPONSE DELAY TIME INTERVAL (sec) | | | |
|---|---|---|---|---|
| | Td | T0.5-90 | T10-90 | T0.5-99 |
| 0kPa | 2.3 | 1.3 | 1.0 | 4.8 |
| 100kPa | 2.8 | 1.5 | 1.1 | 5.0 |
| 200kPa | 3.2 | 1.7 | 1.3 | 5.5 |

FIG. 2

| SAMPLE ENTRANCE PRESSURE | RESPONSE DELAY TIME INTERVAL (sec) | | | |
|---|---|---|---|---|
| | Td | T0.5-90 | T10-90 | T0.5-99 |
| 0kPa | 2.5 | 1.3 | 1.1 | 5.1 |
| 100kPa | 3.5 | 1.6 | 1.3 | 5.1 |
| 200kPa | 4.5 | 2.0 | 1.6 | 6.0 |

FIG. 5

EXHAUST GAS MEASURING SYSTEM

CROSS-REFERENCE TO RELATED APPLICATION

This application claims priority to JP Application No. 2015-244176, filed Dec. 15, 2015, the disclosure of which is incorporated in its entirety by reference herein.

TECHNICAL FIELD

The present invention relates to an exhaust gas measuring system adapted to sample exhaust gas discharged from an internal combustion engine to measure the components or the like of the exhaust gas, and to the like.

BACKGROUND ART

A response delay in an exhaust gas measuring device for an internal combustion engine consists mainly of: a first-order or high-order delay element caused by the structure and/or electronic circuits of the device; and a dead time element including a transfer time interval that is a time interval required for exhaust gas discharged from the internal combustion engine to reach the exhaust gas measuring device.

The response delay is preferably as small as possible, and therefore for example, a delay correction operation disclosed in Patent Literature is used to improve the first-order or high-order delay element.

On the other hand, the dead time element is improved by minimizing not only the length of an exhaust gas circulation path in the exhaust gas measuring device, but the length of a sampling pipe for sampling the exhaust gas of the internal combustion engine to introduce the sampled exhaust gas into the exhaust gas measuring device.

Nevertheless, for example, in the cases such as a comprehensive exhaust gas measuring system using multiple types of exhaust gas measuring devices, due to the difference among the lengths of sampling pipes to the respective exhaust gas measuring devices, in particular, response components affected by dead time elements are not uniform, and without taking measures, it may be difficult to compare respective measurement results.

For this reason, usually, it is adapted to flow reference gas from introduction ports of the sampling pipes, and measure time intervals from the time of the start of the flow to times when the respective exhaust gas measuring devices detect the reference gas (specifically, times when measurement results rise to 50%). In addition, it is also adapted to set the measured time intervals as response delay time intervals (dead time intervals) specific to the exhaust gas measuring device as well as on the basis of the response delay time intervals, correcting the measurement results of the exhaust gas measuring devices for synchronization, and contribute to the comparison of the measurement results and exhaust gas analysis, respectively and correspondingly.

Specifically, by on the basis of the slowest response exhaust gas measuring device, making a correction to delay the measurement result outputs of the other exhaust gas measuring devices, the measurement results of the respective exhaust gas measuring devices are synchronized.

However, as a result of making careful examination in order to further increase measurement accuracy, the measurement results of the respective exhaust gas measuring devices mutually deviated from one another in some cases. The present inventor has first found that the cause for the deviations lies in the fact that when setting the response delay time intervals, the reference gas was flowed from the introduction ports of the sampling pipes at a constant pressure such as 1 atm.

In other words, the present inventor has identified the cause as follows. That is, in actual exhaust gas measurement, pressures inside the sampling pipes vary in response to a variation in the discharge amount of the exhaust gas, or the like. As a result, in response to the pressure variations, the exhaust gas inside the sampling pipes compresses and expands, and the dead time elements and first-order delay elements vary depending on each of the exhaust gas measuring devices. As a result, deviations from the already fixed response delay time intervals occur.

The variation in response delay time interval may cause a problem even when the number of exhaust gas measuring devices is one. For example, in a split flow dilution system, part of exhaust gas is sampled to measure the concentration of a specific component, and when measuring the amount of the specific component, it is necessary to multiply the concentration measured by an exhaust gas measuring device by the flow rate of the exhaust gas discharged at the same time. This is because when doing this, in the conventional system in which a response delay time interval of the exhaust gas measuring device is fixed, a measured flow rate cannot be synchronized, and consequently an error occurs in the measured amount of the specific component.

CITATION LIST

Patent Literature

Patent Literature 1: Japanese Unexamined Patent Publication JP-A 2004-361241

SUMMARY OF INVENTION

Technical Problem

Therefore, it is the principal intended object of the present invention to provide an exhaust gas measuring system capable of more accurately correcting an error in a measurement result caused by the response delay of an exhaust gas measuring device.

Solution to Problem

That is, the exhaust gas measuring system according to the present invention is one including: a sampling pipe that has an introduction port and a lead-out port and is adapted to, from the lead-out port, lead out exhaust gas introduced from the introduction port; one or more types of exhaust gas measuring devices that are connected to the lead-out port and measure predetermined physical quantities related to the exhaust gas flowing through the sampling pipe; and a correction device adapted to correct measurement results by the exhaust gas measuring devices In addition, the exhaust gas measuring system further includes a pressure sensor adapted to measure the pressure inside the sampling pipe, and the correction device corrects errors in the measurement results caused by response delays with the measured pressure by the pressure sensor as a parameter.

More specifically, as the correction device, one that corrects errors in the measurement results caused by dead time elements of the response delays can be cited.

In the exhaust gas measuring system including the multiple exhaust gas measuring devices, the big problem is that the synchronization of the measurement results of the respective exhaust gas measuring devices cannot be kept due to the response delays. In order to solve this, it is desirable that the correction device calculates the response delays of the exhaust gas measuring devices with the measured pressure as the parameter, and corrects the measurement results of the exhaust gas measuring devices to synchronize the measurement results, respectively. As a result, the concentration ratio among respective components in the exhaust gas, which varies every moment, a fuel consumption obtainable from them, and the like can be accurately calculated.

In the exhaust gas measuring system further including a pressure regulating mechanism that is provided in the sampling pipe and adapted to keep pressure downstream of a placement position constant, it is only necessary that the pressure sensor is provided in any position between the introduction port and the pressure regulating mechanism.

In order to improve accuracy, it is desirable that the pressure sensor is provided near the introduction port.

In order to minimize a pressure variation interval to reduce variations in the original response delays, and consequently increase the accuracy of the corrected measurement results, it is preferable that in the exhaust gas measuring system further including a heating type filter unit provided in the middle of the sampling pipe, the pressure regulating mechanism is collaterally provided on a downstream side of the heating type filter unit.

Advantageous Effects of Invention

Such an exhaust gas measuring system can make the errors in the measurement results smaller than before to improve measurement accuracy even when the pressure of the exhaust gas varies.

BRIEF DESCRIPTION OF THE DRAWINGS

FIG. 2 is a diagram illustrating a table in the same embodiment;

FIG. 5 is a table in the same embodiment; and

DESCRIPTION OF EMBODIMENTS

In the following, one embodiment of the present invention will be described with reference to drawings.

Figure 1:
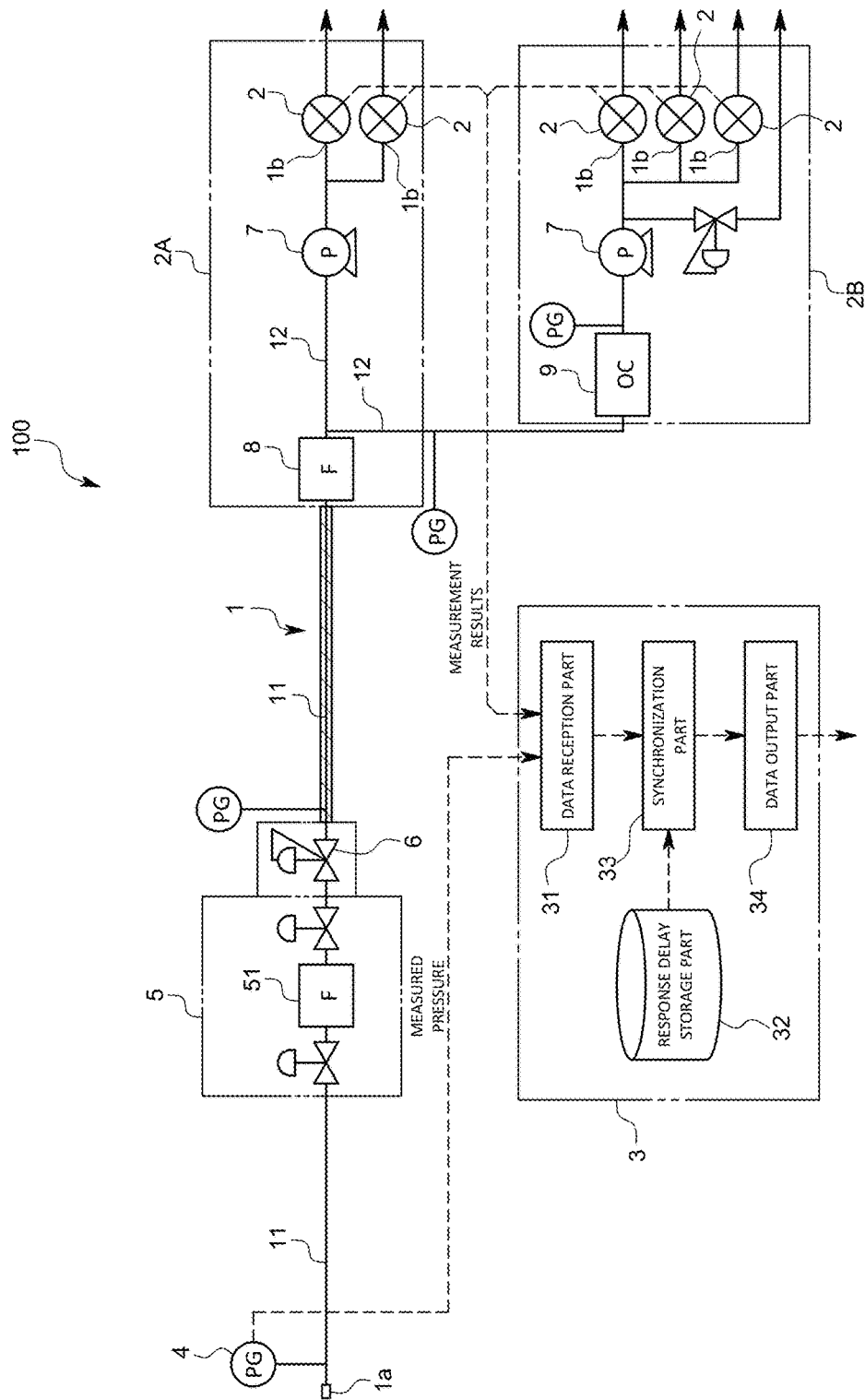
FIG. 1 is a schematic diagram illustrating the whole of an exhaust gas measuring system in one embodiment of the present invention.

An exhaust gas measuring system 100 according to the present embodiment is one adapted to measure the concentrations and amounts of various components contained in exhaust gas discharged from an internal combustion engine of an automobile, and as illustrated in FIG. 1, includes: a sampling pipe 1 for sampling and circulating part of the exhaust gas; multiple types of exhaust gas measuring devices 2 that are connected to the sampling pipe 1 to measure predetermined physical quantities related to the exhaust gas flowing through the sampling pipe 1; and a correction device 3 that performs a predetermined operation on measurement results of the respective exhaust gas measuring devices 2 to synchronize the measurement results with one another.

The respective components will be described.

The sampling pipe 1 is configured to include: a main pipe 11 as a single pipe; and multiple branching pipes 12 branching from the end point of the main pipe 11. The start point of the sampling pipe 1, i.e., the start point of the main pipe 11 is inserted into, for example, the exhaust pipe of the internal combustion engine, and from an introduction port 1a provided at the start point, the exhaust gas is introduced. On the other hand, lead-out ports 1b provided at the end point of the sampling pipe 1, i.e., at the end points of the branching pipes 12, are connected to the exhaust gas measuring devices 2, respectively.

The main pipe 11 is heated by an unillustrated heater and kept at a predetermined temperature in order to prevent dew condensation, THC contamination, and/or the like inside.

Just near the downstream side of the introduction port 1a of the main pipe 11, a pressure sensor 4 for measuring the pressure of the exhaust gas at the introduction port 1a is provided, and also in the middle of the main pipe 11, a heating type filter unit 5 adapted to remove dirt such as dust in the exhaust gas flowing through the main pipe 11 is provided.

The heating type filter unit 5 is one including an unillustrated casing, a first filter 51 contained in the casing, and an unillustrated heater for heating the filter 51 to keep the filter 51 at a predetermined temperature.

At the exit of the heating type filter unit 5, a pressure regulating mechanism 6 (hereinafter also referred to as a regulator 6) is collaterally provided, and thereby it is configured to keep pressure in the sampling pipe 1 on the downstream side of the placement position of the regulator 6 constant.

As the multiple exhaust gas measuring devices 2, ones for measuring the concentrations of various components (such as CO, $CO_2$, $NO_R$, THC, and $H_2O$) contained in the exhaust gas are used, respectively. In this embodiment, these exhaust gas measuring devices 2 are roughly classified into two groups. That is, the two groups include one group that is contained in a heating tank to measure exhaust gas components in a high temperature environment and the other group that measures exhaust gas components at normal temperature. The two groups respectively form exhaust gas measuring units 2A and 2B.

In addition, in FIG. 1, numeral 7 represents a pump for drawing in the exhaust gas, numeral 8 a second filter provided at the entrance of the exhaust gas measuring unit 2A, and numeral 9 an oil catcher for catching oil.

The correction device 3 is one including a CPU, a memory, a communication port, and the like. Also, the CPU and its peripheral devices cooperate in accordance with a predetermined program stored in the memory, and thereby the correction device 3 fulfills functions as a data reception part 31, response delay storage part 32, synchronization part 33, data output part 34, and the like.

Next, the actions of the correction device 3 will be described in combination with the description of the respective parts above.

The data reception part 31 is one that acquires measurement results successively transmitted from the respective exhaust gas measuring devices 2 and a measured pressure successively transmitted from the pressure sensor 4 together with a reception time.

The response delay storage part 32 stores response delays of the exhaust gas measuring devices 2 at each pressure as, for example, a table as illustrated in FIG. 2. A response delay in this embodiment refers to a dead time element, and is mainly caused by a transfer time interval of the exhaust gas from the exhaust gas introduction port 1a to each of the exhaust gas measuring devices 2. This table is preliminarily obtained by experiment or the like.

The table illustrated in FIG. 2 is an example obtained by experiment, and illustrates the relationship between each pressure and a dead time interval Td obtained by experiment using a $CO_2$ concentration measuring device (e.g., NDIR) that is one of the exhaust gas measuring devices 2.

In this experiment, a step response waveform as a measurement result after the introduction of $CO_2$, which is a component gas with a predetermined concentration, into the introduction port 1a as the reference gas is obtained, and from the step response waveform, a dead time interval (hereinafter also referred to as a transfer time interval) Td at each pressure is obtained. The transfer time interval Td is theoretically the time interval required for the measurement result to first reach a value exceeding zero after the introduction of the component gas into the introduction port 1a; however, here, the time interval required for the measurement result to first exceed a concentration corresponding to a certain percentage (such as 5% or 50%) of the predetermined concentration is defined as the transfer time interval Td. It turns out that as the pressure is increased, the dead time interval increases.

Figure 3:
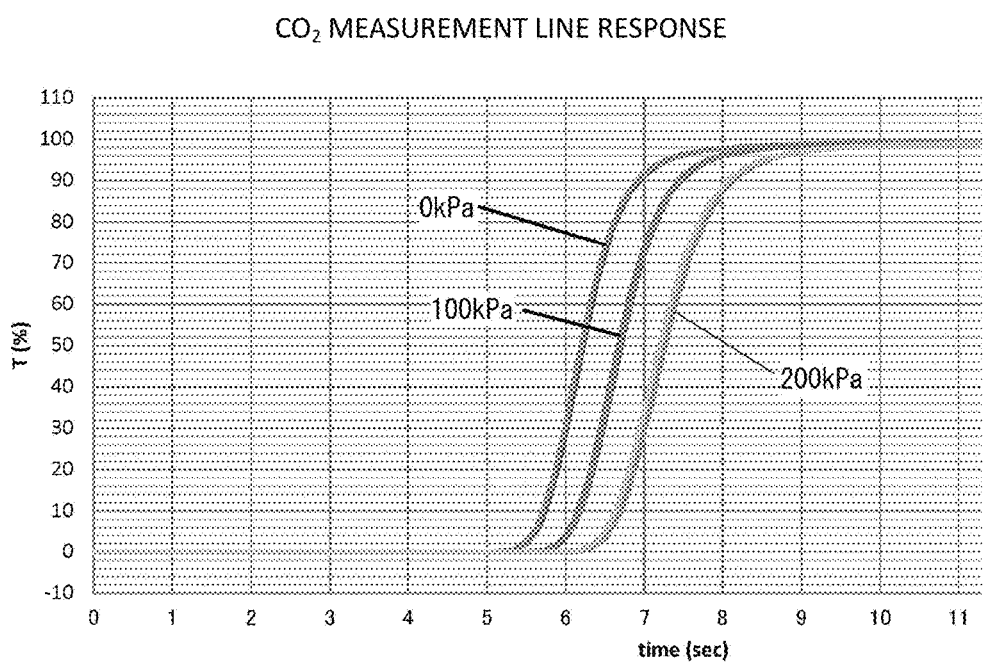
FIG. 3 is a graph illustrating that a response delay varies depending on pressure in the same embodiment.

In addition, FIG. 3 illustrates a graph showing the time-dependent changes of the measurement results in this experiment.

The synchronization part 33 is one that on the basis of the measured pressure, calculates a response delay of each of the exhaust gas measuring devices 2, and on the basis of the response delay, corrects a measurement result of that exhaust gas measuring device 2 successively in real time.

An example of the actions of the synchronization part 33 will be more specifically described while focusing on one of the exhaust gas measuring devices 2. The synchronization part 33 successively acquires the measured pressure, and from the acquired measured pressure, refers to the table in the response delay storage part 32 to calculate a response delay (in this case, a transfer time interval) Td of that exhaust gas measuring device 2.

When performing the calculation, the synchronization part 33 may calculate the response delay Td using the following expression (1) stored in the response delay storage part 32 in place of the table.

$$Td = Td_1 + Td_2 \quad (1)$$

Here, $Td_1$ represents a transfer time interval from the introduction port 1a to the regulator 6, and $Td_2$ represents a transfer time interval from the regulator 6 to the exhaust gas measuring device 2.

$Td_2$ has a constant value not affected by a pressure variation, whereas $Td_1$ is varied in response to the pressure variation and therefore can be expressed as the following expression (2).

$$Td_1 = f(p) \cdot Ts \quad (2)$$

Here, p represents the measured pressure at the introduction port 1a measured by the pressure sensor 4, and f(p) represents a transfer time interval variation coefficient expressed as a function of the measured pressure p. Ts represents a transfer time interval at a reference pressure ps.

The reference pressure ps may be set to, for example, a regulated pressure by the regulator 6.

The synchronization part 33 calculates $Td_1$ by, for example, comparing a molar number of the gas present between the introduction port 1a and the regulator 6 obtained from the measured pressure at the introduction port 1a measured by the pressure sensor 4, a temperature measured by an unillustrated temperature sensor provided in the exhaust gas measuring system 100, and the internal volume of the main pipe 11 from the introduction port 1a to the regulator 6 preliminarily stored in the memory of the correction device 3, and a molar number of the gas sent from the main pipe 11 to the exhaust gas measuring device by the pump 7.

In this case, f(p) can be expressed by, for example, the following expression (3).

$$f(p) = p/ps \quad (3)$$

In expression (3), p represents the measured pressure at the introduction port 1a measured by the pressure sensor 4, and ps is the reference pressure.

f(p) may be one given by a numerical expression, or an experimentally obtained table form, and is, for example, one that is preliminarily stored in the response delay storage part 32 and referred to when the synchronization part 33 calculates $Td_1$.

Using $Td_1$ calculated in this manner and $Td_2$ preliminarily stored in the response delay storage part, the synchronization part 33 calculates the response delay Td on the basis of expression (1) above.

After calculating the response delay Td as described above, the synchronization part 33 obtains a delay time by adding the dead time interval Td to a pressure measurement time when the measured pressure was acquired, and on the assumption that a measurement result of the exhaust gas measuring device 2 received at the delay time is a result actually measured at the pressure measurement time, corrects a measurement time of the measurement result in the exhaust gas measuring device 2 from the reception time. As viewed from a different angle, when making a comparison at the same measurement time, the value of the measurement result is different between before and after the correction.

Note that pressures stored in the table have discrete values, and therefore when the measured pressure has an intermediate value between adjacent discrete values, the synchronization part 33 obtains the response delay by performing an interpolation operation.

In this manner, the synchronization part 33 corrects errors caused by response delays appearing in measurement results of all the exhaust gas measuring devices 2 to synchronize the measurement results, respectively.

Note that the time is not an absolute time but may be a relative time based on, for example, the slowest response exhaust gas measuring device 2. In this case, the synchronization part 33 synchronizes measurement results of the other exhaust gas measuring devices 2 with a measurement result of the slowest response exhaust gas measuring device 2.

Upon request of an operator, the data output part 34 displays and/or outputs a part or all of the measurement results synchronized as described above on a display and/or to a printer as, for example, a graph with the horizontal axis as time.

In such an exhaust gas measuring system, even when the pressure of the exhaust gas varies, the respective measurement results can be synchronized while keeping a smaller error than before, and therefore the concentration ratio among the respective components in the exhaust gas, which varies every moment, and a fuel consumption obtainable from them can be accurately calculated.

Also, in this embodiment, on the uppermost stream side of the sampling pipe 1, i.e., just after the heating type filter unit 5, the regulator 6 is provided to minimize an interval where a pressure variation occurs, and therefore the variation width of a response delay caused by the pressure variation also decreases. Accordingly, the effect of correspondingly decreasing a synchronization error caused by the correction device 3 can also be produced.

Note that the present invention is not limited to the above embodiment.

For example, the above embodiment is adapted to correct the measurement result (more strictly, the measurement time) in consideration of only the dead time element (the transfer time interval) that varies depending on the pressure, but may be adapted to further consider a first-order delay element/a high-order delay element. Specifically, for example, as illustrated in FIG. 2, it turns out that rise time intervals (T0.5-90, T10-90, and T0.5-99 (numerals represent percentages of a saturated value)) related to the first-order delay element/the high-order delay element also vary depending on the pressure. Accordingly, the present invention may correct the measurement result in consideration of the variations in rise time intervals.

To correct the measurement result, the table is referred to, but for example, a correction expression using the pressure as a parameter may be used.

The pressure sensor 4 is only required to be provided in the interval were the pressure varies. In the above embodiment, the pressure sensor 4 is provided just near the introduction port 1a, but may be provided in the middle of the interval. Alternatively, it may be adapted to provide pressure sensors at multiple points and use a pressure gradient as a correction parameter as well.

In the above embodiment, f(p) is one calculated on the basis of the measured pressure measured by the one pressure sensor; however, in order to more accurately calculate f(p) using the pressure gradient as the correction parameter, f(p) may be calculated on the basis of pressure values measured by the multiple pressure sensors provided between the introduction port 1a and the regulator 6.

Figure 4:
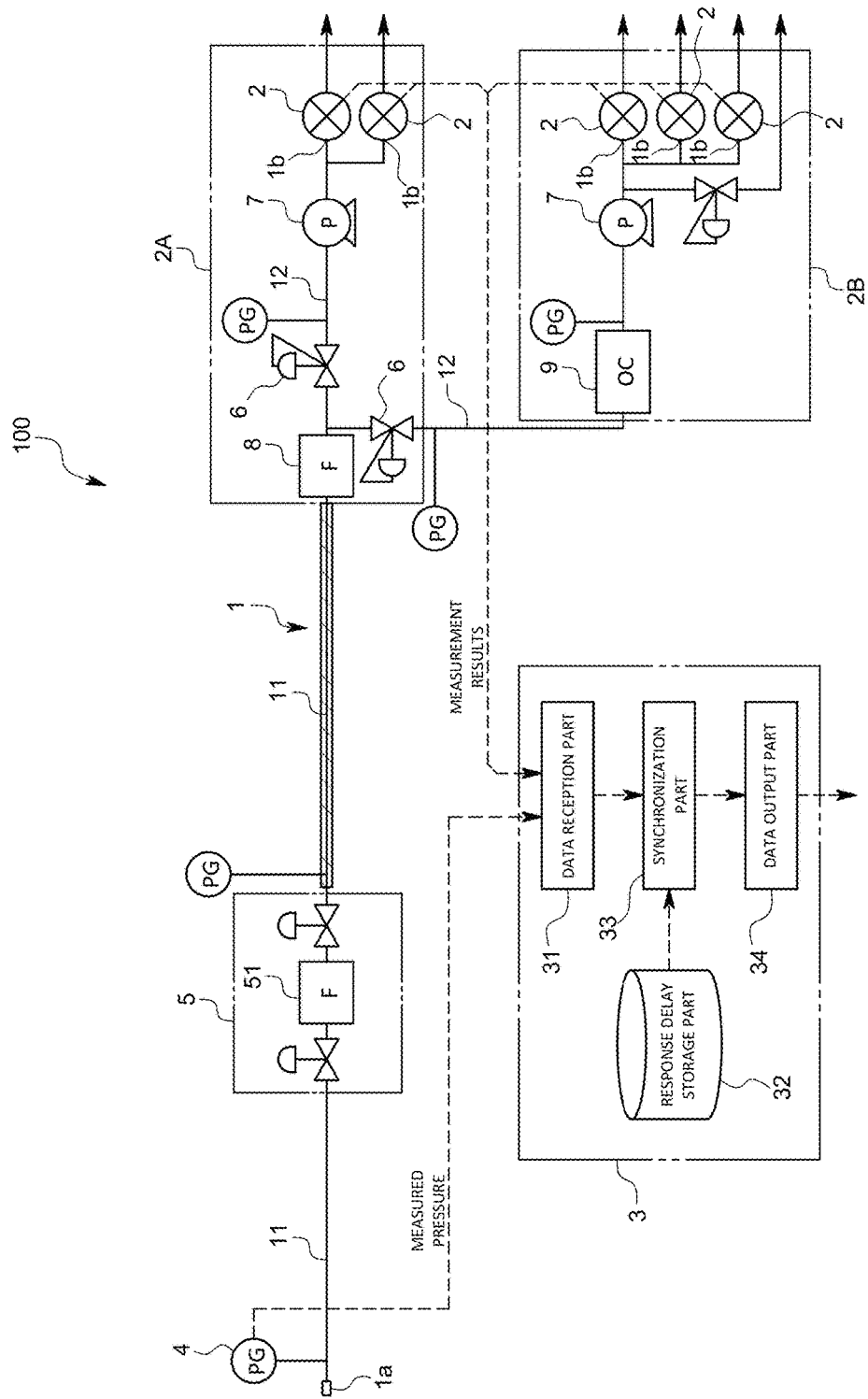
FIG. 4 is a schematic diagram illustrating the whole of an exhaust gas measuring system in another embodiment of the present invention.

The regulator 6 is not necessarily required to be provided at the exit of the heating type filter unit 5. For example, as illustrated in FIG. 4, regulators may be provided in the branching pipes 12, respectively. In this case, it is preferable that the distances from a branching point to the respective regulators 6 are equal to one another.

Figure 6:
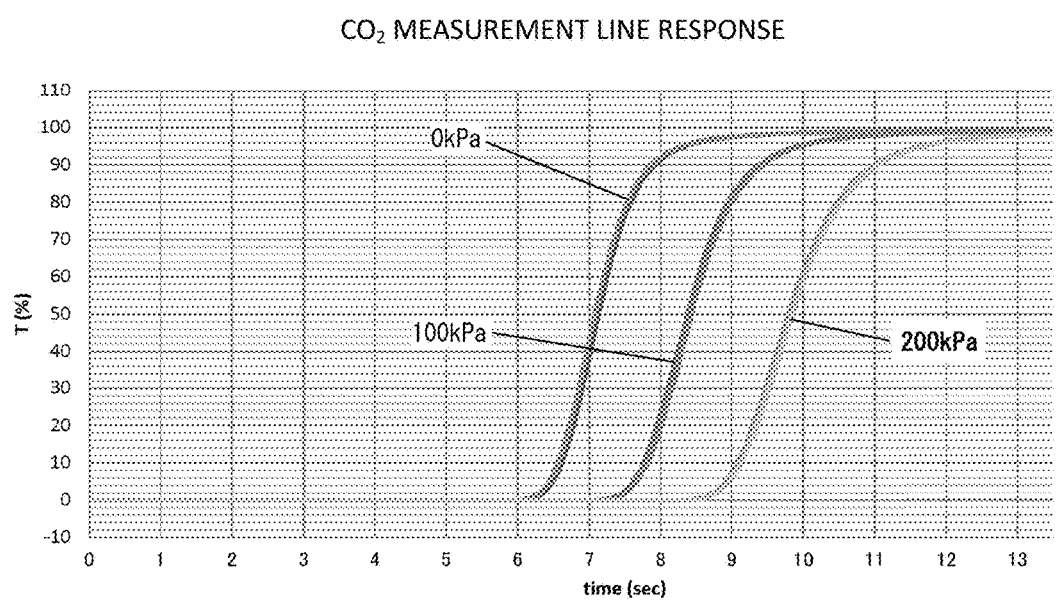
FIG. 6 is a graph illustrating that a response delay varies depending on pressure in the same embodiment.

However, in this configuration, since the pressure variation interval is long as compared with that in the above embodiment, the variation width of a response delay also increases, and even after the correction for synchronization, an error may remain to some extent. Pieces of experimental data on response delays in the configuration of FIG. 4 are illustrated in FIGS. 5 and 6 (respectively corresponding to FIGS. 2 and 3) for reference. It turns out that the variation width of each response delay increases.

The number of exhaust gas measuring devices 2 may be one.

Besides, the present invention may be variously modified or combined without departing from the scope thereof.

REFERENCE SIGNS LIST

100: Exhaust gas measuring system
1a: Introduction port
1b: Lead-out port
1: Sampling pipe
2: Exhaust gas measuring device
3: Correction device
4: Pressure sensor
5: Heating type filter unit
6: Pressure regulating mechanism (regulator)

What is claimed is:
1. An exhaust gas measuring system comprising:
a sampling pipe that has an introduction port and a lead-out port and is adapted to, from the lead-out port, lead out exhaust gas introduced from the introduction port;
a pressure sensor adapted to measure pressure inside the sampling pipe;
one or more types of exhaust gas measuring sensors that are connected to the lead-out port and measure predetermined physical quantities related to the exhaust gas flowing through the sampling pipe; and
a processor adapted to correct errors in measurement results of the exhaust gas measuring sensors, caused by pressure-dependent transfer time intervals associated with the exhaust gas flowing from the introduction port to the one or more types of exhaust gas measuring sensors, on a basis of response delays estimating the pressure-dependent transfer time intervals and calculated from the pressure measured by the pressure sensor to synchronize the measurement results, respectively.

2. The exhaust gas measuring system according to claim 1, further comprising a pressure regulator that is provided in the sampling pipe and adapted to keep pressure downstream of a placement position constant, wherein
the pressure sensor is provided between the introduction port and the pressure regulator.

3. The exhaust gas measuring system according to claim 2, further comprising a heating type filter provided in a middle of the sampling pipe, wherein
the pressure regulator is collaterally provided on a downstream side of the heating type filter.

4. The exhaust gas measuring system according to claim 1, wherein
the pressure sensor is downstream the introduction port.

5. The exhaust gas measuring system according to claim 1, wherein the response delays are stored in a response delay storage part.

6. A correction method applied to an exhaust gas measuring system including a sampling pipe that has an introduction port and a lead-out port and is adapted to, from the lead-out port, lead out exhaust gas introduced from the introduction port, and one or more types of exhaust gas measuring sensors that are connected to the lead-out port and measure predetermined physical quantities related to the exhaust gas flowing through the sampling pipe, the method comprising:
measuring pressure inside the sampling pipe with a pressure sensor; and
correcting errors in measurement results of the exhaust gas measuring sensors, caused by pressure-dependent transfer time intervals for the exhaust gas to flow from the introduction port to the one or more types of exhaust gas measuring sensor, on a basis of response delays estimating the pressure-dependent transfer time intervals and calculated from the pressure measured by the pressure sensor to synchronize the measurement results, respectively.

7. The correction method according to claim 6 further comprising storing the response delays in a response delay storage part.

8. A recording medium that stores a program applied to an exhaust gas measuring system including a sampling pipe that has an introduction port and a lead-out port and is adapted to, from the lead-out port, lead out exhaust gas introduced from the introduction port, a pressure sensor adapted to measure pressure inside the sampling pipe, one or more types of exhaust gas measuring sensors that are connected to the lead-out port and measure predetermined physical quantities related to the exhaust gas flowing through the sampling pipe, and a processor, the program instructing the processor to fulfill a function of correcting errors in the measurement results of the exhaust gas measuring sensors, caused by pressure-dependent transfer time intervals for the exhaust gas to flow from the introduction port to the one or more types of exhaust gas measuring sensors, on a basis of response delays estimating the pressure-dependent transfer time intervals and calculated from the pressure measured by the pressure sensor to synchronize the measurement results, respectively.

9. The recording medium of claim 8, wherein the program further instructs the processor to fulfill a function of storing the response delays in a response delay storage part.

\* \* \* \* \*